United States Patent [19]

Rebuffat et al.

[11] Patent Number: 4,966,602
[45] Date of Patent: Oct. 30, 1990

[54] COMPRESSION DEVICE FOR THE ANASTOMOSIS OF HOLLOW ORGANS

[76] Inventors: Carlo Rebuffat, Largo Corsia dei Servi, 11; Riccardo Rosati, Via Livorno, 4, both of Milano, Italy

[21] Appl. No.: 413,312

[22] Filed: Sep. 27, 1989

[30] Foreign Application Priority Data

Sep. 28, 1988 [IT] Italy ................ 22096 A/88

[51] Int. Cl.⁵ ............................................. A61B 17/00
[52] U.S. Cl. ...................................... 606/154; 604/153
[58] Field of Search ............................ 606/154, 153

[56] References Cited

U.S. PATENT DOCUMENTS

| | | | |
|---|---|---|---|
| 3,974,835 | 8/1976 | Gottardy, Jr. .................. | 606/154 |
| 4,467,809 | 8/1984 | Hardy et al. .................... | 606/154 |
| 4,552,148 | 11/1985 | Hardy, Jr. et al. ............. | 606/154 |
| 4,598,712 | 7/1986 | Rebuff et al. ................... | 606/153 |

Primary Examiner—Randall L. Green
Assistant Examiner—Gary Jackson

[57] ABSTRACT

A compression device for the anastomosis of hollow organs comprising three members having a hollow cylinder shape suitable to compress the edges of the hollow organs that are to be anastomosized. Each one of these members is formed by sectors that remain solidly connected to one another until the edges of the hollow organs are present, and separate into fragments when the edges break off from the seat of anastomosis, as they, necrotizing, lose their consistency.

12 Claims, 3 Drawing Sheets

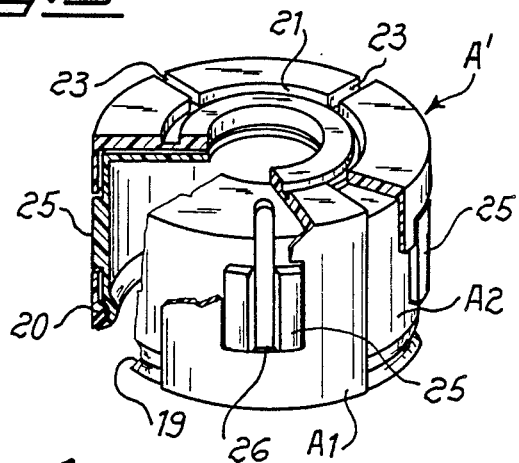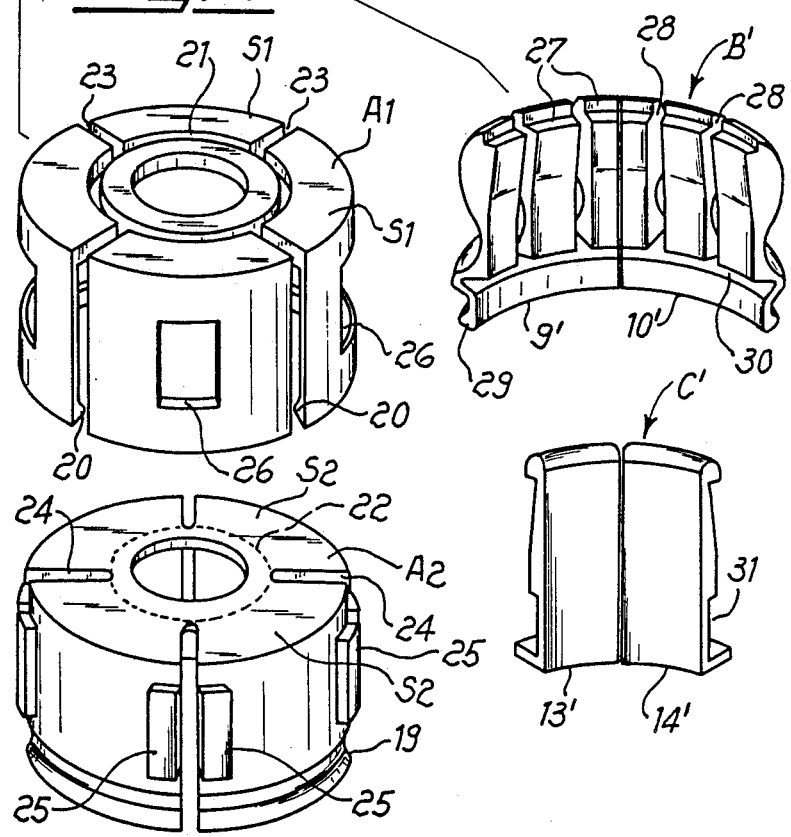

COMPRESSION DEVICE FOR THE ANASTOMOSIS OF HOLLOW ORGANS

BACKGROUND OF THE INVENTION

The present invention relates to a compression device for the anastomosis of hollow organs of the human body, such as parts of the digestive tract.

The use in organs such as the, esophagus of the conventional suture techniques, conventional suturing threads or clipping, is nevertheless affected by a high percentage of immediate and delayed complications, and therefore it has been proposed to use compression devices to carry out the anastomosis of said organs. These devices keep the edges to be anastomosized juxtaposed by compressing their ends. After a certain time has elapsed, outside the compression area a "natural" anastomosis is achieved and the device, consequently to the necrosis of the compressed edges, breaks off and falls inside the intestine, from which it is then evacuated together with the stool. The use of said devices is however at present limited to the most distal tracts of the intestine. In fact, the anatomical arrangement of the organs of the most cranial part of the digestive tract makes it impossible to use these devices due to the great difficulty that, after breaking off from the site of anastomosis, they would encounter in passing such structures as the pylorus sphincter and the ileocecal valve, that are low caliber segments of the digestive tract.

Devices have thus been introduced, the parts of which that are suitable to compress in between the terminal parts of the hollow organs to be connected are made of biodegradable material, whereby said devices are reduced into fragments that can then be more easily expelled with the stool.

This technique is known for example from U.S. Pat. No. 3,974,835.

The biodegradation rate of said materials varies from individual to individual, and within the same individual according to the different physiological condition implying alteration of the methabolism and, therefore, a change in the rate of the chemical reaction causing the biodegradation. There is therefore a problem in that it can not be precisely forecast how long time will be necessary for the fragments of said devices to be reduced: in fact, it might even occur before or long time after the natural consolidation of the edges of the organs to be anastomized. In both cases disadvantageous conditions would be created: in the first case the surgery would have failed because the holding device would have been fragmented in advance relative to the consolidation, that is no healing of the organs to be anastomized would occur, and in the second case an obstacle would be introduced into the digestive tract in an unforeseable seat and for a longer time than necessary.

Moreover, said devices made of biodegradable material must necessarily have thin walls, thereby exhibiting the draw-back of being very fragile and difficult to manufacture.

It is the purpose of the present invention to eliminate the above-mentioned drawbacks by providing a device exhibiting the following advantages:

it is reduced into fragments as soon as the edges of the organs that have been compressed by the device members lose their consistency, that is certainly after the same breaks off from the anastomosis, and therefore after its healing, it can be made of any material, even a hard one.

A further purpose of the present invention is to provide a device that can be manufactured at a favourable price.

SUMMARY OF THE INVENTION

All of the above purposes are achieved by the title device, which comprises a first member having a hollow cylinder shape and suitable to contain a second member having a hollow cylinder shape as well, whereby between said two members the edges of said two hollow organs to be anastomosized can be inserted, and a third member having a hollow cylinder shape that is suitable to press the second member against the first one, thereby compressing the edges of said hollow organs, characterized in that each of said three members consists of sectors that are provided with suitable means to keep said sectors solidly connected to one another until said edges are present between the first and second members and separate into fragments when said edges lose their consistency.

BRIEF DESCRIPTION OF THE DRAWINGS

Further features and advantages of the invention will be evident from the following detailed description of two preferred but non exclusive embodiments of the subject device, said embodiments being shown in a merely illustrative, non limiting way in the enclosed figures, in which:

FIG. 3 is a perspective view of the first member of the second embodiment; and

FIG. 4 is an exploded, partly cross-sectional view of the members of the second embodiment.

DESCRIPTION OF THE PREFERRED EMBODIMENTS

Referring now to the figures, the subject device comprises a first member A having a hollow cylinder shape in which a second member B having a hollow cylinder shape is housed, and a third member C having a hollow cylinder shape that, when it is inserted into member B, applies a pressure against the same.

Figure 2:
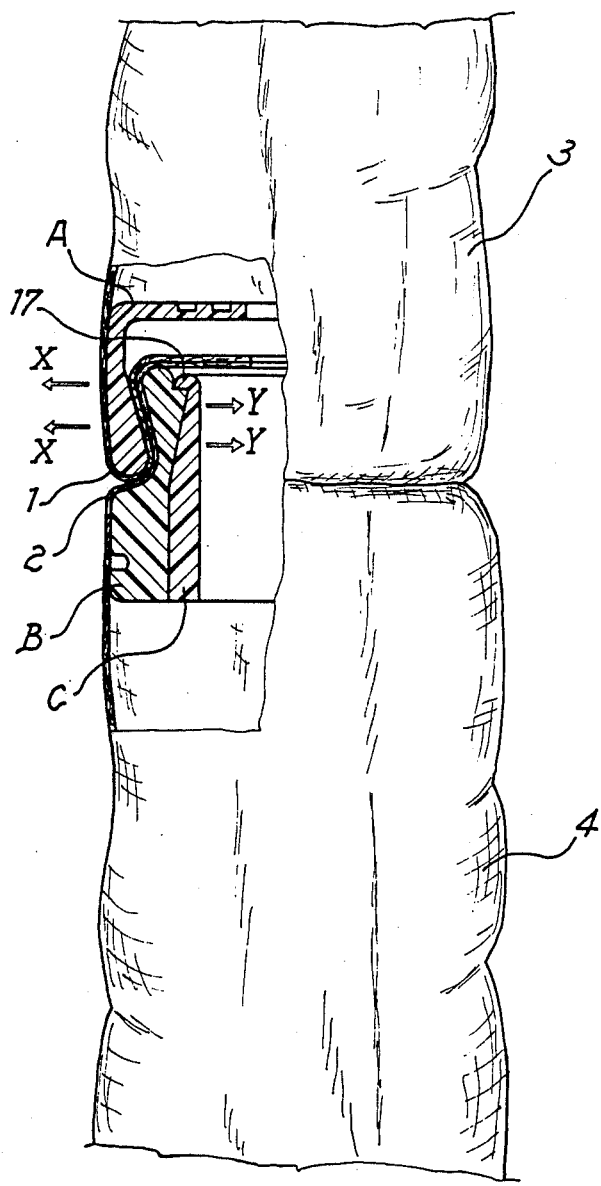
FIG. 2 is a vertical section view of the subject device applied to the hollow organs to be anastomized.

In this way, referring to FIG. 2, edges 1 and 2 of the hollow organs 3 and 4 of the digestive tract that are to be anastomized, which are enclosed between the first and second members A and B, are compressed therebetween. Members A, B and C are inserted into the hollow organs 3 and 4 by means of suitable equipment, one of which, for example, is described in the italian patent No. 1,173,284 filed Feb. 16, 1984.

According to the present invention each of members A, B and C comprises sectors that are provided with releasable joining means that are suitable means to keep said sectors solidly connected to one another until said edges are present between the first and second members and separate when said edges, that by that time are necrotized, after the device breaks off from the seat of anastomosis, lose their consistency by the action of the gastric juice. Therefore, this occurs after the anastomosis has been consolidated, whereby the fragmentation of the device is not affected by chemical reactions, as it occurs, on the contrary, in the device of the prior art.

Figure 1:
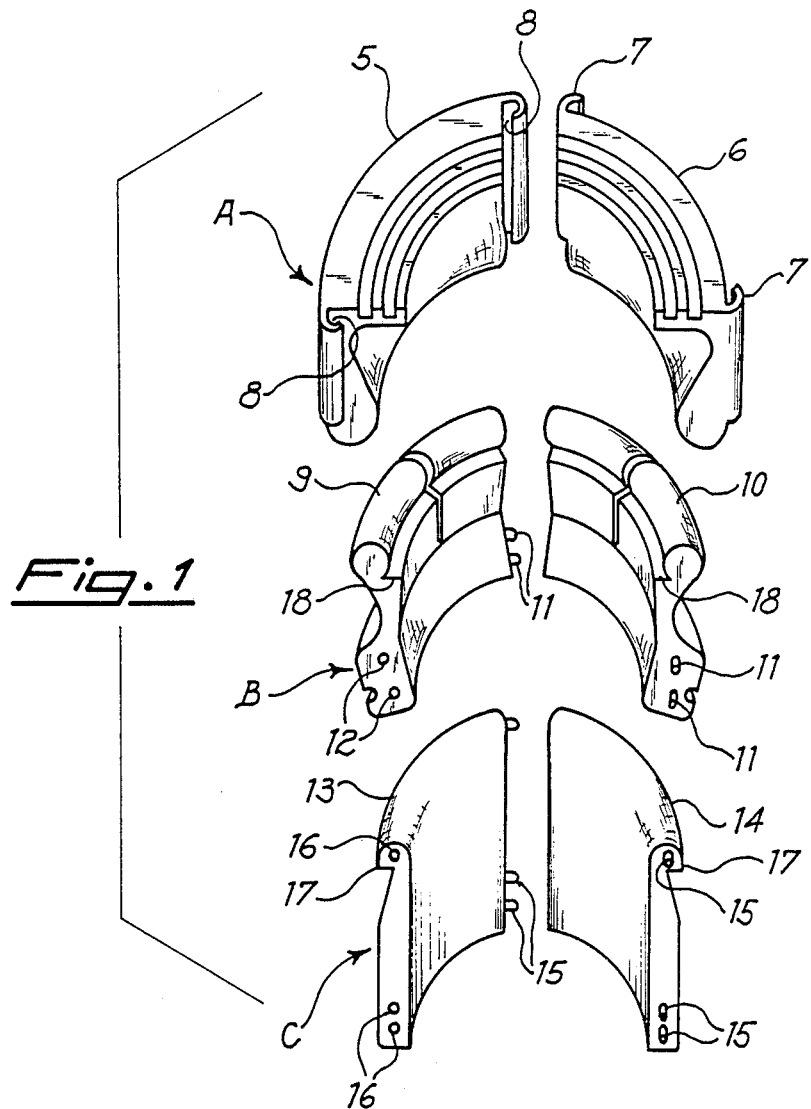
FIG. 1 is an exploded, partly cross-sectional view of the members of the first embodiment.

More precisely, as can be seen in FIG. 1, member A comprises sectors 5, 6, similar sectors, not shown, completing the hollow cylindrical shape of member A. Sector 6 is provided on its terminal edges with protrusions 7 projecting outwards, while the adjacent sector 5 is provided at its terminal edges with cavities 8 that are open inwards, whereby each of cavities 8 engages with a protrusion 7 of the adjacent sector. In a similar way, member B comprises sectors 9 and 10, like sectors, not shown, completing the hollow cylindrical shape of member B. Each sector is provided at a terminal edge with pins 11 and at the other terminal edge with holes 12, whereby the pins 11 of each sector engage with holes 12 of the adjacent sector. In a like manner, member C comprises sectors 13, 14, similar sectors, not shown completing the hollow cylindrical shape of member C. Each sector is provided at one of its terminal edges with pins 15 and at other one with holes 16, whereby the pins 15 of each sector engage with holes 16 of the adjacent sector.

The above-mentioned cavities and protrusions, as well as the pins and corresponding holes, are the joining means between adjacent sectors. The sectors of each member A, B and C can amount to whatever number greater than two. To perform the anastomosis surgery, the edges 1 and 2 of the hollow organs to be anastomized are inserted between the hollow members A and B, pressed by hollow member C that is arranged inside member B with the circumferential projecting part 17 of member C inserted into the circumferential groove 18 of member B. Until edges 1 and 2 are intertwined between members A and B, the sectors the members A, B and C are comprised of are solidly connected. This is due to the pressure said edges apply onto member A according to arrows X and onto members B and C according arrows Y (the direction of which is opposite) and acting onto said joining means between sectors in such a way as to keep members A, B and C as if they were a single rigid piece. As soon as the anastomosis is consolidated, just outside of the compression area, the device including edges 1 and 2 breaks off from its seat, edges 1 and 2 necrotize and lose their consistency, whereby said pressures are released, and the connection between sectors as well, whereby the sectors of the three members are separated and reduced into fragments that, being freely movable inside the digestive tract, are thus expelled with the utmost ease.

The second embodiment is shown in FIGS. 3 and 4, wherein the parts that are similar to those shown in FIGS. 1 and 2 are denoted by the same, primed symbols. This embodiment is suitable to further facilitate manufacturing and assembling the members that are to compress the edges of the hollow organs.

First member A', in particular, comprises two sub-members A1 and A2 that engage with one-another by means of undercut 19 that is inserted into protrusion 20, the latters being arranged in the lower circumferential part of sub-members A1 and A2, respectively. Member A' is therefore a compact, easy-to-handle member that can be easily applied to an apparatus, such as, for example, the apparatus described in the above-mentioned italian patent No. 1,173,284, that permits the subject device to be positioned and employed.

At the moment said apparatus is employed, a circular blade of the apparatus dissects the sub-members A1 and A2 along groove 21 and circumference 22, respectively, whereby, due to the radial slots 23, 24 provided in the upper part of said sub-members A1 and A2, the latter ones are automatically fragmented to four sectors S1 and four sectors S2.

When the edges 1, 2 of hollow organs 3 and 4 are inserted between members A' and B', in a similar way as shown in FIG. 2, said sectors S1 and S2, when there is a pressure between member A' and member B', which is similar to member B of FIG. 1, remain solidly connected to each other by means of teeth 25 that are provided on the circumferential part of sectors S2 of sub-member A2, said teeth engaging in windows 26 that are provided of the circumferential part of sectors S1 of sub-member A1.

In FIG. 3, member A', comprising sub-members A1 and A2 fixed to each other by means of undercut 19, said undercut being provided on sub-member A2 that receives the protrusion 20, which is provided on sub-member A1, and of teeth 25 that are engaged with windows 26, is clearly shown. Said teeth 25 do not protrude from windows 26; member A', therefore, has a completely smooth outer appearance, with no protrusion. This is due to the fact that the thickness of the teeth is same as that of the windows.

Member B' comprises sectors 9' and 10', that are similar to sectors 9 and 10 previously described in the illustration of FIG. 1. In said sectors 9' and 10' an increased flexibility has been obtained, in that they are shaped according to fins 27 by slots 28, extending downwards as far as base 29, the internal part of which contains the circumferential groove 30. Member C', consisting of sectors 13' and 14', that is forced against member B', is similar to member C of FIG. 1, the difference therefrom being the groove 31 that is provided in its lower outer part for it to be better adapted to base 29 of member B'.

Changes can be brought to the invention, especially to the structure of the above-mentioned joining means, without departing from the scope of the invention as defined in the claims.

We claim:

1. A compression device for the anastomosis of hollow organs, comprising: a first member having a hollow cylinder shape and suitable to contain a second member having a hollow cylinder shape as well, whereby between said two members the edges of said two hollow organs to be anastomosized can be inserted, and a third member having a hollow cylinder shape that is suitable to press the second member against the first one, thereby compressing the edges of said hollow organs, characterized in that each of said three members consists of sectors that are solidly connected to one another until said edges are present between the first and second members and separate into fragments when said edges necrotize.

2. A compression device according to claim 1, characterized in that means are provided at the terminal edges of each sector in such a way as to provide a releasable connection between adjacent sectors.

3. A compression device according to claim 2, characterized in that the first member comprises sectors each of which is provided at one of its terminal edges with a protrusion projecting outwards, the adjacent sector being provided on the adjacent terminal edge with a cavity opening inwards, into which said protrusion is inserted, thus providing said releasable connection.

4. A compression device according to claim 2, characterized in that both the second and third members comprise sectors each of which is provided at one of its terminal edges, with one or more holes and the other adjacent sector is provided at its adjacent terminal edge with one or more pins suitable to be inserted into said holes, thereby providing said releasable connection.

5. A compression device according to claim 1, characterized in that the first member comprises two sub-members that engage with each other, said sub-members being provided on their upper part with radial slots, so that with the use of a known apparatus for positioning said compression device a circular blade of said apparatus dissects the two sub-members, thus fragmenting them to sectors.

6. A compression device according to claim 5, characterized in that said sub-members are engagingly joined to each other by means of an undercut and a protrusion that are provided in the lower circumferential part of said sub-members.

7. A compression device according to claim 5, characterized in that the circumferential parts of said sub-members are provided with teeth and windows, respectively, that engagingly connect to one another.

8. A compression device according to claim 7, characterized in that said teeth protrude from the sub-member that is inserted into the other sub-member provided with said windows.

9. A compression device according to claim 8, characterized in that the thickness of the teeth is the same as that of the windows, thereby causing the outer wall of said first member to be completely smooth, with no protrusion.

10. A compression device according to claim 1, characterized in that the sectors of the second member are provided with fins formed by slots that are provided on the cylindrical part of said second member and extending downwards to the base of the second member, so as to enhance the flexibility of the sectors.

11. A compression device according to claim 10, characterized in that said base is provided in its internal part with a circumferential groove.

12. A compression device according to claim 11, characterized in that the sectors of the third member have a circumferential groove in their lower outer part that is adapted to the base of the second member.

* * * * *